United States Patent [19]
Takeuchi et al.

[11] Patent Number: 5,396,813
[45] Date of Patent: Mar. 14, 1995

[54] GAS PASSAGE SHIFTING DEVICE

[75] Inventors: Minoru Takeuchi, Hokkaido; Mitsunori Shimada, Shizuoka, both of Japan

[73] Assignee: Nikkiso Company Limited, Tokyo, Japan

[21] Appl. No.: 208,389

[22] Filed: Mar. 10, 1994

Related U.S. Application Data

[63] Continuation-in-part of Ser. No. 721,521, Jul. 12, 1991, abandoned.

[30] Foreign Application Priority Data

Aug. 31, 1989 [JP] Japan .................................. 1-225859

[51] Int. Cl.6 .......................... G01N 7/04; F16J 15/46
[52] U.S. Cl. ...................................... 73/865.5; 73/37; 285/97; 277/34
[58] Field of Search ...................... 73/37, 865.5, 37.5; 277/34, 34.3, 47, 183, 201, 214; 285/96, 97, 138, 139, 374

[56] References Cited

U.S. PATENT DOCUMENTS

| 3,211,007 | 10/1965 | Atkins | 73/865.5 |
| 3,603,138 | 9/1971 | Peterson | 73/37 |

FOREIGN PATENT DOCUMENTS

| 0829509 | 1/1952 | Germany | 285/97 |
| 58-206947 | 12/1983 | Japan . | |
| 63-238446 | 10/1988 | Japan . | |

Primary Examiner—Hezron E. Williams
Assistant Examiner—Michael J. Brock
Attorney, Agent, or Firm—Browdy & Neimark

[57] ABSTRACT

A novel gas passage shifting device used primarily for a surface area measuring apparatus for particulate materials is disclosed. The device is characterized by having a base member provided with a recess which receives a tubular body so as to gas-tightly connect it to the gas passage by a simple operation.

3 Claims, 5 Drawing Sheets

GAS PASSAGE SHIFTING DEVICE

CROSS REFERENCE TO THE COPENDING APPLICATION

This is a continuation-in-part application of Ser. No. 07/721,521, filed Jul. 12, 1991, now abandoned.

FIELD OF THE INVENTION

The present invention relates to a gas passage shifting device, a sealing member and a mounting device for tubular members; more specifically to a gas passage shifting device, a sealing member and a mounting device for tubular member for a surface area measuring apparatus for particulate materials.

BACKGROUND OF THE INVENTION

As shown in FIG. 5, the hitherto known conventional surface area measuring apparatus for particulate materials generally comprises a first conduit 1, a second conduit 2 and a third conduit 3; a gas meter means A interposed midway in the first conduit 1; another gas meter means B interposed midway in the third conduit 3; a first U-shaped sample cell 4 detachably connected to the terminal of the first conduit 1 at one end thereof and also detachably connected to the starting point of the second conduit 2 at the other end thereof; and a second sample cell detachably connected to the terminal of the second conduit 2 at one end thereof and also detachably connected to the starting point of a third conduit 3 at the other end thereof.

The surface area of a sample is measured by such an apparatus in the following manner.

The sample is placed in the second sample cell 5 and the cell is connected to the terminal of the second conduit 2 and the starting point of the third conduit. The first sample cell 4 is also connected to the terminal of the first conduit 1 and the starting point of the second conduit 2. Then the second sample cell is heated to a high temperature and a deaerating gas is passed through the first conduit, the first sample cell, the second conduit, the second sample cell and the third conduit and thereby slight amounts of moisture and adsorbed gases in the sample in the second sample cell 5 are removed. After this deaeration has been continued for a predetermined period of time, the two sample cells are detached from the conduit line, the second sample cell 5 is connected to the terminal end of the first conduit at one end and to the starting end of the second conduit 2 at the other end and the first sample cell is connected to the terminal of the second conduit 2 at one end and to the starting point of the third conduit 3 at the other end. Thereafter, a measuring gas, which is a mixture of an inert gas and nitrogen, is passed through the first conduit 1, the second sample cell 5, the second conduit 2, the first sample cell 4 and the third conduit 3 while the second sample cell 5 is chilled with liquid nitrogen so that the nitrogen is adsorbed on the sample.

While this operation is being carried out, the gas flow detected at the gas meter means A is larger than that detected at the gas meter means B. When the sample is saturated with the nitrogen, the gas flows detected by the gas meter means A and the gas meter means B become equal. Then chilling of the second sample cell 5 is discontinued while the flow of the gas mixture is maintained and the temperature of the second sample cell returns to room temperature.

As the temperature of the second sample cell rises, the adsorbed nitrogen is gradually desorbed and the gas flow detected at the gas meter means B becomes larger than that detected at the gas meter means A. The amount of the adsorbed nitrogen can be measured by integrating the increasing gas flow.

The surface area of the sample can be calculated from the amount of the adsorbed nitrogen.

With a surface area measuring apparatus of this structure, exchange of the first sample cell 4 and the second sample cell 5 in the conduit system is necessary.

The reason why the first sample cell 4 and the second sample cell 5 must be exchanged is that a heating means and a chilling means are required.

In order to make the apparatus a closed system, the first sample cell 4 is required in addition to the second sample cell 5. This increases the number of apparatus parts and makes the operation more complicated.

Therefore, a surface area measuring apparatus, which does not require surplus parts such as the first sample cell 4 as shown in FIG. 6, is known.

In this apparatus as shown in FIG. 6, a conduit 6 for deaerating gas is connected to a three-way valve 7; a conduit 8 for measuring gas is connected to the three-way valve 7 via a first gas meter means A and a second three-way valve 9; the remaining outlet of the first three-way valve 7 is communicated to the inlet of the sample cell 11 via conduit 10; the outlet of the sample cell 11 is communicated to another three-way valve 13 via a conduit 12: one outlet of the third three-way valve 13 is communicated to a first exhaust conduit 14; the remaining outlet of the third three-way valve 13 is communicated to a fourth three-way valve 15 and to a second exhaust conduit 16 via a fourth three-way valve 15 and another gas meter means B; the second three-way valve 9 and the fourth three-way valve 15 are communicated to each other by means of the remaining outlets via a conduit 17.

When deaeration is carried out with this apparatus, the ports (1) and (2) of the first three-way valve 7 are communicated, the ports (2) and (3) of the second three-way valve 9 are communicated, the ports (1) and (2) of the third three-way valve 13 are communicated and the ports (3) and (1) of the fourth three-way valve 15 are communicated, and thus a passage is formed from the conduit 6 for deaeration gas to the exhaust conduit 14 via the three-way valve 7(1)(2), the sample cell, the three-way valve 13(1)(2).

A deaeration gas is passed through the sample cell 11 which contains a sample, while the measuring gas is passed through the first gas meter means A, the second three-way valve 9(2)(3), the conduit 17, the fourth three-way valve 15(3)(1), the second gas meter means B and the exhaust conduit 16.

After the deaeration is finished, the three-way valves 7, 9, 13 and 15 are switched over so that the measuring gas passes through the first gas meter means A, the second three-way valve 9(2)(1), the first three-way valve 7(3)(2), the sample cell 11, the third three-way valve 13(1)(3), the fourth three-way valve (2)(1), the second gas meter means B and the exhaust conduit 16.

In an apparatus, in which a plurality of three-way valves are employed, however, the switch-over of the three way valves is complicated and troublesome and the operation of such an apparatus is apt to be accompanied by danger of operation error.

Further, conventional surface area measuring apparatuses are not free from gas leakage at the part where the sample cell is mounted. In other words, in conventional apparatuses, perfect mounting of the sample cell is not easy.

DISCLOSURE OF THE INVENTION

The present invention was completed under the circumstances.

The object of the present invention is to solve the above-described problems and other problems relating to the surface area measuring apparatus for particulate materials.

The object of the present invention is to provide a gas passage shifting device, which is suitably applied to a surface measuring apparatus and to which a sample cell can be easily mounted perfectly gas-tight. More specifically, the object of the invention is to provide a gas passage shifting device of simple structure, which enables shifting of deaeration gas and measuring gas by simple operation without possibility of operation error and well secures gas-tightness.

Another object of the present invention is to provide a seal member, which is able to hold a tubular body such as a sample cell gas-tight.

Still another object of the present invention is to provide a device for mounting a tubular body.

In order to achieve the above-described object, in the gas passage shifting device for surface area measuring apparatus which measures surface area or specific surface area of a particulate material by deaerating a sample in the sample cell, thereafter measuring the amount of the gas supplied into the sample cell and the amount of said gas exiting the sample cell and thus learning the amount of the gas adsorbed on the sample, the gas passage measuring device of the present invention comprises:

- a gas inlet which is connected to one end of a first gas passage provided with a first gas meter means, a second gas inlet which is connected to one end of a fourth gas passage connected to the outlet of a sample cell at the other end, a third gas inlet which is connected to one end of a second gas passage provided with a second gas meter means, a first outlet which is connected to the other end of the second gas passage, a second gas outlet which is connected to a fifth gas passage exhausting gas, and a third gas outlet which is connected to one end of a third gas passage connected to the inlet of the sample cell at the other end;
- a rotary valve which communicates the first gas inlet and the first gas outlet, the second gas inlet and the second gas outlet, and the third gas inlet and the third gas outlet when the sample is deaerated; and communicates the first gas inlet and the third gas outlet, the second gas inlet and the first gas outlet, the third gas inlet and the second gas outlet when measurement is carried out;
- a base member provided with a first recess which is provided at the position corresponding to the inlet of the sample cell and provided with an opening communicating with the third gas passage in the center thereof and a groove surrounding the opening at the bottom, a second recess which is provided at the position corresponding to the outlet of the sample cell and provided with an opening communicating with the fourth gas passage in the center thereof and a groove surrounding the opening at the bottom and an air supply means for supplying air into the first and second recesses;
- seal members respectively attached to the first recess and the second recess, which respectively comprise a cylindrical part with an annular end inserted into said groove, a bore to receive the cylindrical tube part of the sample cell, a circumferentially formed thinned portion and a flange provided at the bottom of the cylindrical part and tightly contacting the base member, at least said thinned portion being made of a resilient and extendible material; and
- a member for fixing the seal member to the base member, which secures the base disc part 62 of the seal member 60 to the base member; wherein
- said base member, said seal member and said fixing member consitutes a mouting device for a tubular member.

In the gas passage shifting device in accordance with the present invention, the base member is usually a thick plate. A rotary valve is used, which shifts the gas passages.

In the deaeration operation, a gas passage is formed, which comprises the first conduit, the first gas meter means, the first gas inlet, the first gas outlet, the second gas meter means, the second conduit, the third gas inlet, the third gas outlet, the third conduit, the sample cell, the fourth conduit, the second gas inlet, the second gas outlet and the fifth conduit.

By passing a deaeration gas through this passage, deaeration of the sample is effected.

After the deaeration of the sample, the gas passage is shifted, by the operation of the rotary valve, to the one comprising the first conduit, the first gas meter means, the first gas inlet, the third gas outlet, the third conduit, the sample cell, the fourth conduit, the second gas inlet, the first gas outlet, the second gas meter means, the second conduit, the third gas inlet, the second gas outlet and the fifth conduit.

The measuring gas is passed through this passage for adsorption by the sample.

The gas passage can be easily shifted by simple operation of the rotary valve, which enables speedy gas passage shift without possibility of operation error.

The mounting of the sample cell is carried out as follows.

The seal members are secured to the first recess and the second recess. The annular end portion of the cylindrical part thereof is inserted into the groove provided in the bottom of the first recess and the flange thereof is tightly secured to the base member. The cylindrical tube part of the sample cell is inserted into the bore of the seal member until the opening of the tube contacts the bottom of the first recess. The diameter of the bore may be equal to or slightly larger than the outside diameter of the cylindrical tube. The reason why the former may be larger than the latter is that the thinned portion of the seal means tightly contacts the outer surface of the cylindrical tube by expansion as described below and the passage of gas is prevented. If the diameter of the bore and the outside diameter of the cylindrical tube is equal, the gas-tight contact required when the cylindrical tube is inserted into the bore is better effected.

There flange of the seal member can be tightly secured to the base member by means of an adhesive or by means of a fixing member as in the present invention.

An example of materials for the seal member, which is required to be elastic and lubricious, is silicone rubber.

In the same manner as the above described, the other cylindrical tube of the sample cell is fixed to the second recess.

When the cylindrical tubes of the sample cell are fixed to the first and second recesses, respectively a space is formed by the outside surface of the cylindrical part of the seal member, the bottom of the recess, the inside wall of the recess and the flange. Into this space, air for sealing is introduced via air passage. Thereby the above-described thinned portion is expanded inward and tightly contacts the surface of the cylindrical tube of the sample cell. By this tight contact, the sample cell can be tightly secured to the base member. the air, which is apt to penetrate into the gas passage through the butted part of the cylindrical tube and the opening of the gas passage, is prevented.

The sample cell is held gas-tight by means of the continued introduction of the pressurizing air all through the time when the surface area measurement is carried out.

The pressurizing air for sealing is introduced into the recesses through the gas hole provided in the wall of the recesses.

BRIEF DESCRIPTION OF THE ATTACHED DRAWINGS

PREFERRED EMBODIMENT OF THE INVENTION

Now the invention will be specifically described in detail by way of a working example. However, the invention is not limited to this embodiment but the invention can be worked in various modes as long as they do not deviate from the gist of the invention, needless to say.

This example relates to a gas passage shifting device mounted on a surface area measuring apparatus for particulate materials.

Figure 1:
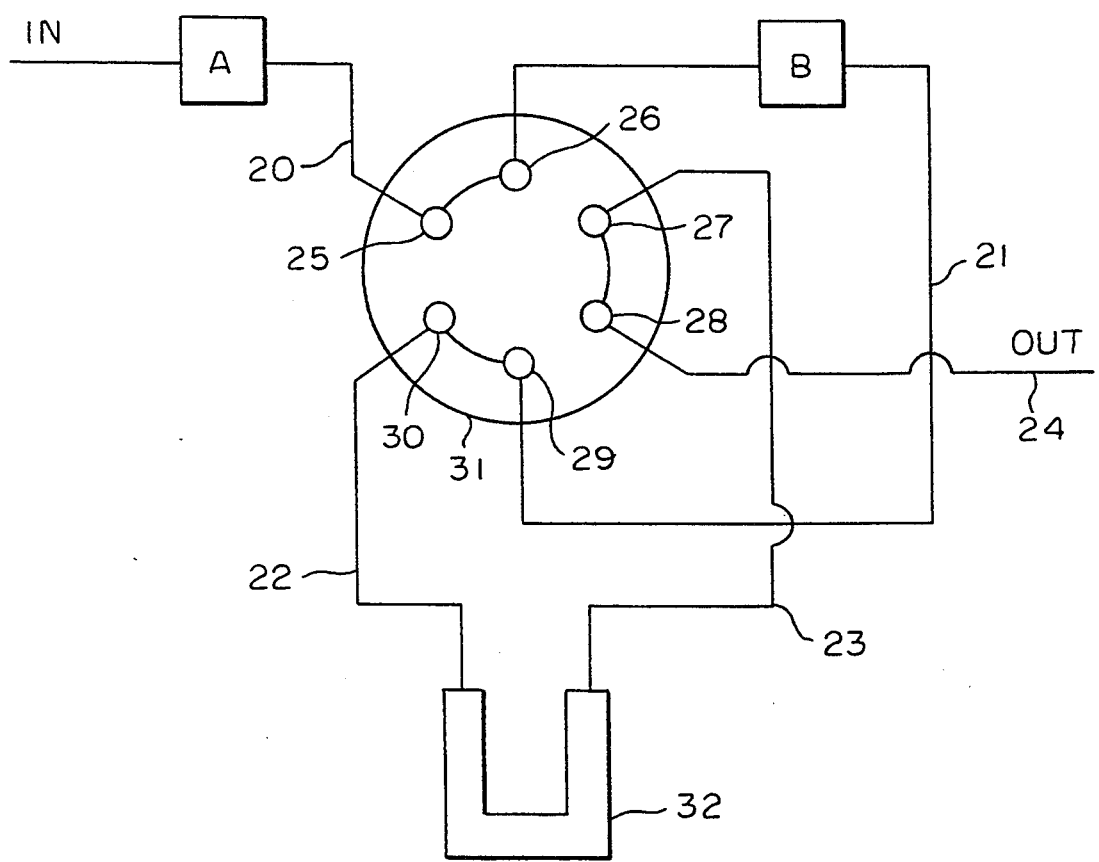
FIG. 1 is a schematic representation of an example of the gas passage shifting device of the present invention, wherein a gas passage is in the state of deaerating operation.
Figure 2:
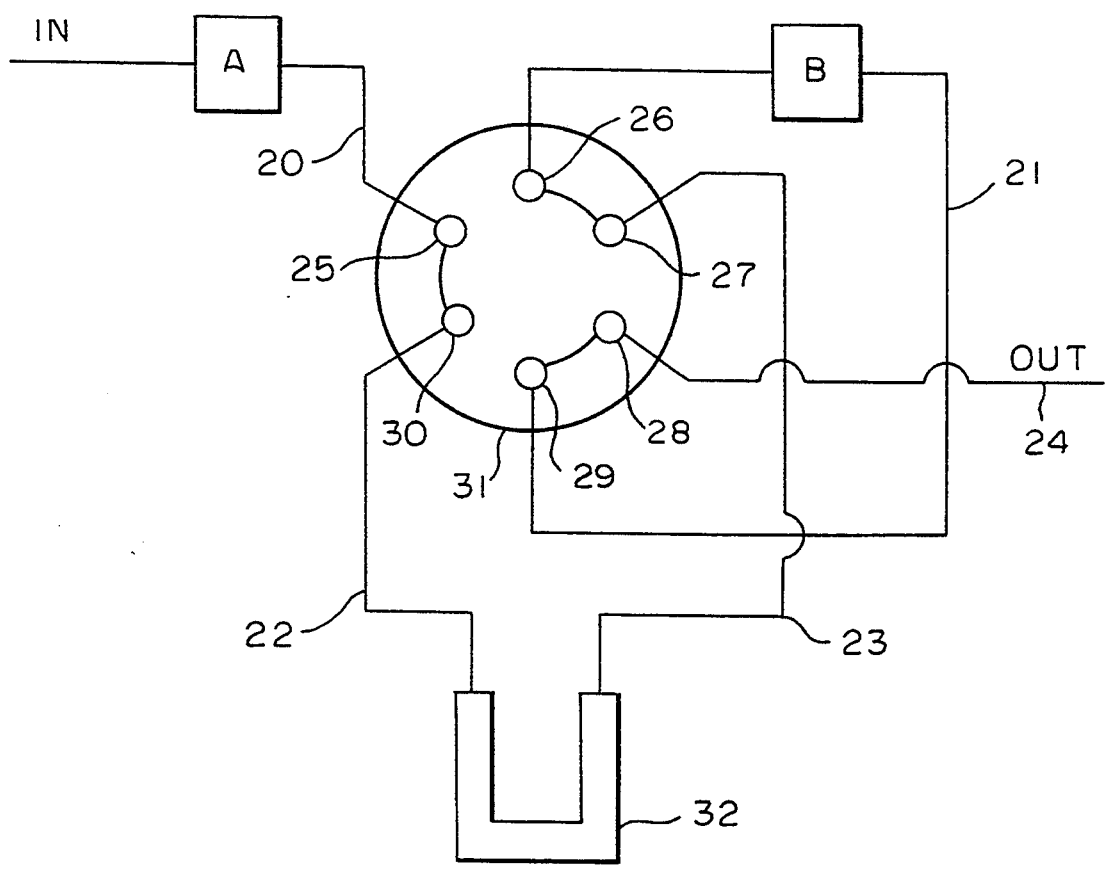
FIG. 2 is a schematic representation of the same example of the gas passage shifting device of the present invention, wherein the gas passage is in the state of passing a measuring gas.

As shown in FIG. 1 or 2, this gas passage shifting device comprises a first gas passage 20, a second gas conduit 21, a third gas passage 22, a fourth gas passage 23, a fifth gas passage 24; a rotary valve 31 provided with a first gas inlet 25, a first gas outlet 26, a second gas inlet 27, a second gas outlet 28, a third gas inlet 29, and a third gas outlet 30; a first gas meter means A and a second gas meter means B.

The gas meter means A is provided midway in the first gas passage 20, the terminal end of the first gas passage 20 is connected to the first gas inlet 25 of the rotary valve 31.

The gas meter means B is provided midway in the second gas passage 21, one end of the second gas passage 21 is connected to the second gas outlet 26 of the rotary valve 31 and the other end is connected to the third gas outlet 29.

One end of the third gas passage 22 is connected to the third gas outlet 30, and the other end thereof is connected to the inlet of a sample cell 32.

One end of the fourth gas passage 23 is connected to the outlet of the sample cell 32 and the other end thereof is connected to the second inlet 27.

One end of the fifth gas passage 24 is connected to the second gas outlet 28.

Figure 3:
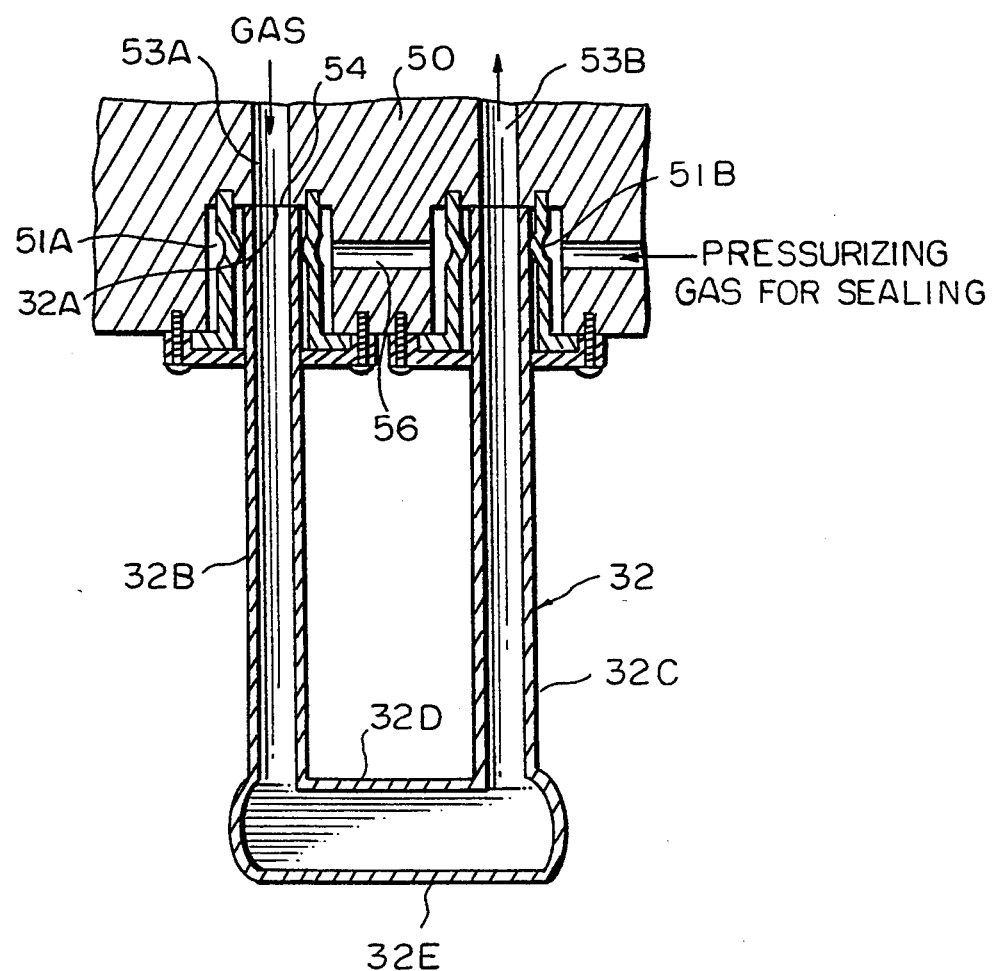
FIG. 3 is a cross-sectional view of a base member and a sample cell fixed thereto.

The sample cell 32 is connected to the third gas passage 22 and the fourth gas passage 23 as shown in FIG. 3.

Figure 4:
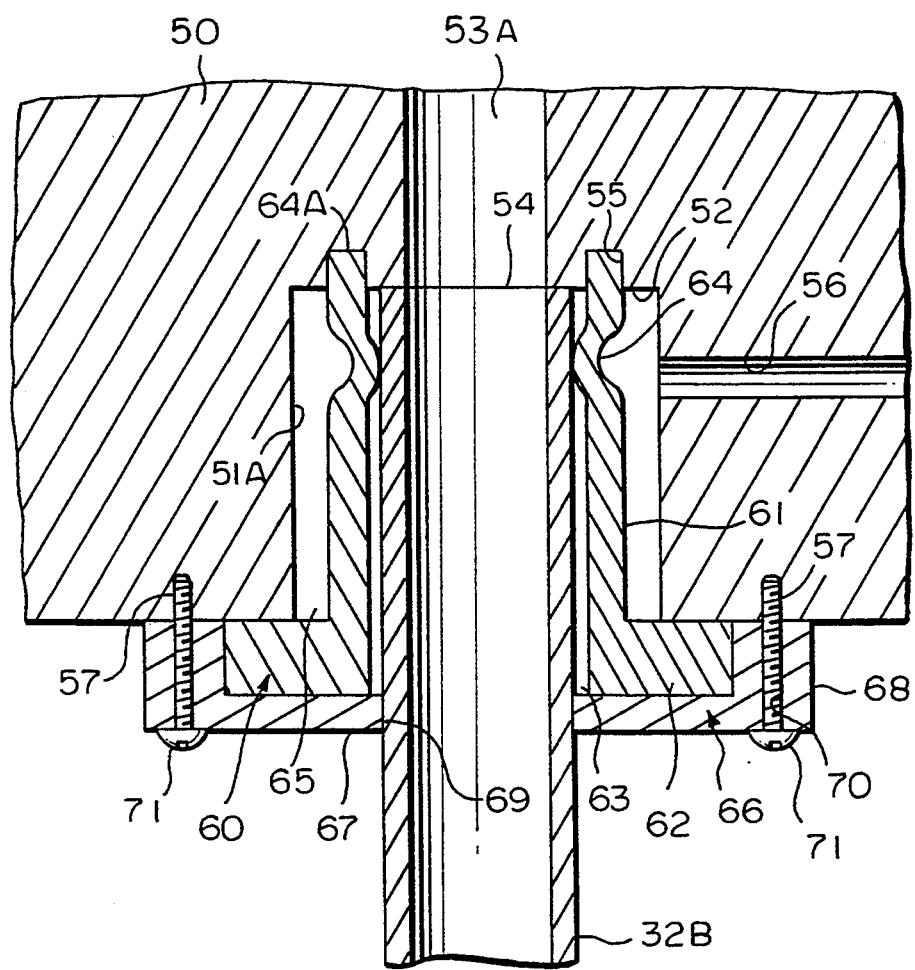
FIG. 4 is a further enlarged cross-sectional view of the sample cell which is fixed to the base member via a seal member.
Figure 5:
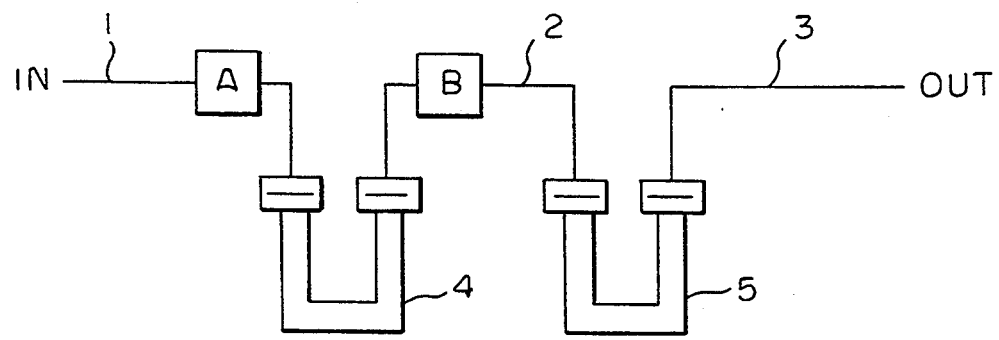
FIG. 5 is a schematic representation of a surface area measurement apparatus with a conventional gas passage shifting device.
Figure 6:
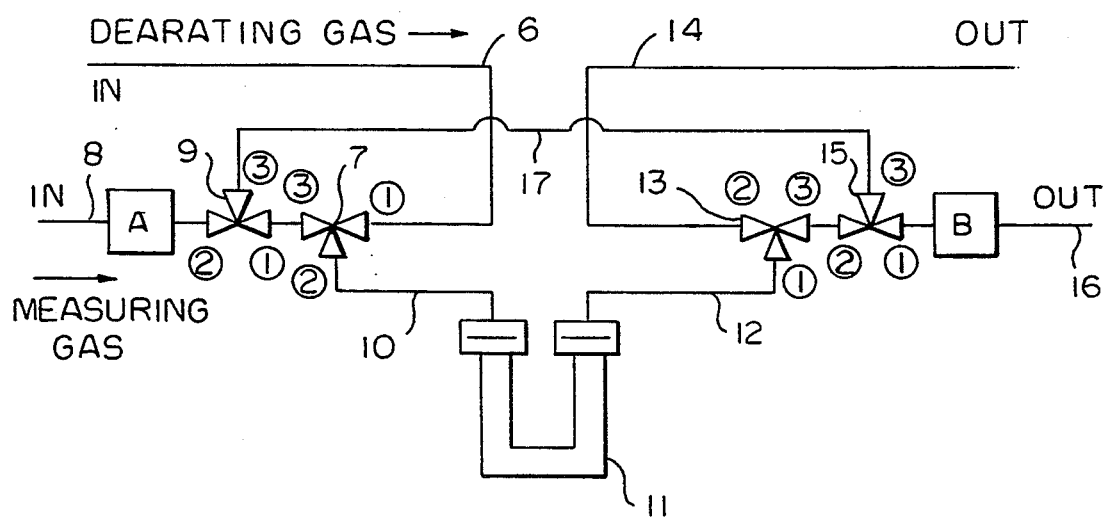
FIG. 6 is a schematic representation of a suraface area measurement apparatus with another conventional gas passage shifting device.

FIG. 3 is an enlarged cross-sectional view showing the sample cell fixed to a base member. FIG. 4 is a further enlarged cross-sectional view showing the part where one end of the sample cell is connected to the base member using a seal member.

As shown in FIG. 3, the base member 50 has a structure as described below so that the sample cell 32 can be fixed thereto so as to communicate with the third gas passage 22 and the gas passage.

The sample cell 32 is generally of U shape, which comprises a first upright cylindrical tube 32B having an opening 32A at one end thereof, which is to be inserted into a seal member described below; a second upright cylindrical tube 32C, which has the same diameter and length as those of the first upright tube 32B, has an opening to be inserted into a seal member in the same manner as the first cylindrical tube 32A and a sample-receiving tube 32D, which has the central axis which crosses the central axes of the first cylindrical tube 32B and the second cylindrical tube 32C at a right angle. The sample cell 32 has a flat bottom 32E so that it can stand stable.

The base member 50 has a first cylindrical recess 51A and a second cylindrical recess 51B at the underside thereof. The two recesses have parallel central axes.

The first recess 51A has an inside diameter larger than the outside diameter of the seal member, which is described later. At the ceiling 52 of the first recess 52A, a first fluid passage 53A is provided. The opening 54 of this first fluid passage 53A has an inside diameter the same as that of the above-mentioned first cylindrical tube 32B. The first fluid passage 53A is gas-tightly connected to the third gas passage 22 as a through hole. An annular groove 55 is provided around the opening 54 at the ceiling 52 of the first recess 51A. This groove has a width enough to tightly receive the end portion of the cylindrical part of the seal member described below. The depth of this groove is suitably decided by considering sealing effect. A communication passage 56 is provided in the base member, said passage communicating the first recess 51A and the second recess 51B as shown in FIG. 3. The base member is also provided with screw holes 57 for securing a fixing member as described later.

In this embodiment, the first recess 51A and the second recess 51B are provided on the underside of the base member 50. When the base member 50 is viewed from underside, the bottoms of the recesses 51A and the recess 51B are ceilings as mentioned above. In the specification, however, these surfaces are designated as bottom 52 hereinafter for the convenience of description. In this embodiment, the recess 51A and the recess 51B are provided on the underside of the base member 50 and the first cylindrical tube 32B and the second cylindrical tube 32C are inserted into the first recess 51A and the second recess 51B. However, it is possible to provide the first recess 51A and the second recess 51B on the top of the base member 50, and to insertor mount the cylindrical tube 32B and the cylindrical tube 32B from above. Therefore, there is no problem in designating the surface 52 of the first recess 51A and the second recess 51B, where the fluid passages open, as bottom.

The seal member 60 comprises a cylindrical part 61 and a flange 62, which extends from the bottom end of the cylindrical part 61. The opening 63 of the seal member 61 at the flange 62 receives the first cylindrical tube 32B or the second cylindrical tube 32C. In the cylindrical part 61, a thinned constricted portion 64 is provided near the end opposite to the flange. That is, a thin inside beading is formed round the inside wall of the cylindrical part. The inside diameter of the ridge line of the beading 64 of the cylindrical part 61 preferably should be substantially the same as that of the outside diameter of the cylindrical tube 32 of the sample cell 32. At least the beading portion of the seal member 60 must be made of a resilient and preferably extendible material and preferably has a smooth surface, since the cylindrical tube 32B or 32C of the sample cell 32 must be inserted into the cylindrical part 61 and it must be expanded toward the inside. An example of such materials is silicone rubber.

The end 64A opposite to the flange of the cylindrical part of the seal member 60 is inserted into the annular groove 55 provided at the above-mentioned bottom surface 52.

The outside diameter of the flange 62 is larger than the diameter of the opening of the first recess 51A and the second 51B. This outside diameter of the flange 62 is determined so that sufficient gas-tight contact is effected between the flange 62 and the surface of the base member in order to confine air in the space 65 formed by the outside surfaces of the seal member 60 of the seal member 60 and the inside surfaces of the first recess 51A or the second recess 51B.

As will be understood from the above detailed description, the seal member 60 in this embodiment has a shape like a silk hat without the top. By way of precaution, it is added that the seal member is not necessarily of a silk-hat-like shape.

This seal member 60 is secured to the underside of the base member 50 by means of a fixing member 66. In this embodiment, a device for mounting a sampling cell is constructed with the recess 51A or 51B of the base member, the fixing member 66 and the seal member 60.

There is no limitation in the shape of the fixing member 66 as long as it is able to press the flange 62 of the seal member 60, which is fixed to the first recess 51A or the second recess 51B, toward the underside surface of the base member 50, and secures the gas-tight contact of the flange 62 and the underside surface of the base member 50. In this embodiment, it comprises an annular wall part 68 and a base disc part 67. The base disc part is provided with a hole 69 in the center thereof, said hole having a diameter large enough to receive the cylindrical tube 32A or 32B of the sample cell 32. The above-mentioned annular wall 68 is provided upright at the periphery of the base disc part 67. The height of the annular wall 68 from the base disc part is determined so as to be a little smaller than the thickness of the flange 62. The annular wall 68 has a plurality of through holes 70 at the positions corresponding to the screw holes 57 provided in the underside of the base member 50, the fixing member 66 is secured to the underside surface of the base member 50 by inserting a screw into each through hole 70 and screwing it into each screw hole 57. When the fixing member 60 is secured to the underside of the base member 50, the base disc part 66 of the fixing member 66 is pressed onto the flange 62 of the seal member 60 and the screws 71 are inserted into the through holes 70 and screwed into the screw holes 57 at the underside of the base member. Thus the flange 62 of the seal member 60 can be tightly pressed onto the underside surface of the base member 50. The first cylindrical tube 32B is inserted into the first recess 51A through the hole 69 after the flange 62 has been tightly pressed onto the underside surface of the base member 50.

The insertion of the first cylindrical tube 32B is carried out until the opening 32A of the first cylindrical tube 32B reaches the bottom surface 52 of the recess 51A.

As has been described in detail in the above, the first cylindrical tube 32B and the second cylindrical tube 32C are inserted into the first recess 51A and the second recess 51B via the seal member 60. In this state, a space is formed by the flange 62, the outside surface of the cylindrical part 61 of the seal member 60 and the bottom surface 52 of the first recess 51A and the second recess 51B respectively as has been described. From an air supply source (not shown in the drawings), air is introduced into the second recess 51B and further in the first recess 51A via the communication passage 56. Then the constricted portion 64 expands toward the first cylindrical tube 32A and is tightly pressed onto the surface of the first cylindrical tube 32B. By this tight contact, the air introduced into the space 65 and the air present in the outside of the first cylindrical tube 32B are prevented from flowing out through the butted part between the opening 54 of the first cylindrical tube 32B and the fluid passage 53A. The situation is just the same with the second recess 51B.

According to this embodiment, the sample cell 32 can be instantly connected to the third gas passage 22 and the fourth gas passage 23 by a simple operation and that the connection is tight and reliable.

In the gas passage shifting device including the above-described sample cell connecting structure, gas passages are connected as shown in FIG. 1 when the deaerating operation is carried out by heating the sample cell 32 by means of a mantle heater or the like.

In this deaerating operation, the first gas meter means A and the second gas meter means B are not used.

When the sample cell 32 is chilled with a Dewar bottle containing liquid nitrogen or the like and measuring gas is passed therethrough for adsorption of nitrogen or the like, a gas passage circuit as shown in FIG. 2 is formed by the operation of the rotary valve 31.

As apparent from the above description, the gas passage shift is easily effected by operation of the rotary valve.

Any known rotary valve can be used in the present invention.

Industrial Utility

The present invention provides a gas passage shifting device which is of simple structure comprising fewer device parts, easy in shifting of the deaerating gas passage and the measuring gas passage by means of a rotary valve and free from possibility of operation error.

Because the shifting of the gas passages can be easily effected by operation of a rotary valve, there is no need to detach the sample cell and, therefore, the operator is released from the troublesome operation.

Further, in the present invention, seal members are used, which not only enables connecting of the sample cell to the gas passages by a simple operation but also secures tight and reliable connection. Also fixing of seal members can be effected easily and securely.

What we claim is:

1. In a surface area measuring device for measuring a surface area or a specific surface area of a sample by measuring an amount of gas adsorbed on the sample from an amount of the gas supplied to a sample cell and an amount of the gas discharged from the sample cell after the sample cell containing the sample has beed deaerated, comprising a gas passage shifting device adapted to be connected to a sample cell, the improvement wherein the gas shifting device comprises:

a rotary valve comprising a first gas inlet, a first gas outlet, a second gas inlet, a second gas outlet, a third gas inlet and a third gas outlet;

the rotary valve further comprising means for shifting between a first position and a second position, the first position simultaneously connecting the first gas inlet with the first gas outlet, the second gas inlet with the second gas outlet, and the third gas inlet with the third gas outlet; the second position simultaneously connecting the first gas inlet to the third gas outlet, the first gas outlet to the second gas inlet, and the second gas outlet to the third gas inlet;

a first gas passage leading to the first gas inlet; a second gas passage extending between the first gas outlet and the third gas inlet; a third gas passage extending between the third gas outlet and a connector with which the third gas passage is connected to a first end of the sample cell; a fourth gas passage extending between the second gas inlet and the connector with which the fourth gas passage is connected to a second end of the sample cell; and a fifth gas passage extending from the second gas outlet; and a first gas flow measuring means located along the first gas passage, and a second gas flow rate measuring means located along the second gas passage;

the connector comprising a base member and seal members;

the base member provided with a first recess which is provided at the position corresponding to the first end of the sample cell and provided with an opening communicating with the third gas passage in the center thereof and a groove surrounding the opening at the bottom, a second recess which is provided at the position corresponding to the second end of the sample cell and provided with an opening communicating with the fourth gas passage in the center thereof and a groove surrounding the opening at the bottom and an air supply means for supplying air into the first and second recesses;

the seal members respectively attached to the first recess and the second recess, which respectively comprise a cylindrical part with an annular end inserted into the groove, a bore to receive a cylindrical tube part of the sample cell, a circumferentially formed thinned portion and a flange provided at the bottom of the cylindrical part and tightly contacting the base member, at least the thinned portion being made of a resilient end extendible material.

2. A seal member comprising: a cylindrical part having an annular end which is inserted into a groove provided around an opening of a gas passage at the bottom of a recess of a base member to which pressurizing air for sealing is introduced, said cylindrical part having a bore for receiving a tubular body to be communicated to said gas passage and a thinned portion circumferentailly provided in the wall thereof; and a flange which is provided at the other end of said cylindrical part, has a larger diameter than the diameter of said recess and is to be tightly secured to the surface of the base member.

3. A mounting device comprising: a base member having a recess provided at the position where a tubular body is secured, said recess having an opening communicating with a gas passage at the bottom thereof, a groove surrounding said opening and another opening for introducing a gas for sealing; a seal member comprising a cylindrical part, which has an annular end to be inserted into the groove, and a flange which is provided at the bottom of the cylindrical part and has a larger diameter than the diameter of the recess and a bore to receive the tubular body which is to be communicated with the gas passage; and a fixing means which secures the flange of the seal member inserted into the recess to the surface of the base member.

* * * * *